United States Patent [19]

Roesky et al.

[11] Patent Number: 6,156,948
[45] Date of Patent: Dec. 5, 2000

[54] METHOD FOR PREPARATION OF STYRENES

[75] Inventors: Rainer Roesky, St. Quentin Fallavier, France; Holger Borchert, Bockenheim a.d. Weinstrasse; Uwe Dingerdissen, Seeheim-Jungenheim, both of Germany

[73] Assignee: Aventis Research & Technologies GmbH & Co. KG, Frankfurt, Germany

[21] Appl. No.: 09/355,307

[22] PCT Filed: Jan. 17, 1998

[86] PCT No.: PCT/EP98/00244

§ 371 Date: Jul. 27, 1999

§ 102(e) Date: Jul. 27, 1999

[87] PCT Pub. No.: WO98/32719

PCT Pub. Date: Jul. 30, 1998

[30] Foreign Application Priority Data

Jan. 19, 1997 [DE] Germany .............. 197 03 111

[51] Int. Cl.⁷ .............. C07C 1/20; C07C 1/32; C07C 1/207
[52] U.S. Cl. .............. 585/437; 585/436
[58] Field of Search ............... 585/436, 437

[56] References Cited

U.S. PATENT DOCUMENTS

| 3,636,182 | 1/1972 | Kallos et al. | 260/604 |
| 3,893,948 | 7/1975 | Khcheyan et al. | 252/440 |
| 3,927,133 | 12/1975 | Satomura | 260/669 QZ |
| 4,120,909 | 10/1978 | Amirnazmi | 260/668 R |

FOREIGN PATENT DOCUMENTS

| 2317525 | 4/1973 | Germany . |
| 486005 | 1/1975 | U.S.S.R. . |
| 538353 | 1/1941 | United Kingdom . |
| 616844 | 1/1949 | United Kingdom . |

OTHER PUBLICATIONS

Abstract No. XP–002064376, pp. 881–882, 1985 ( No English ).
Periodic Table of the Elements (SArgent–Welch Scientic Company) 1979.

Primary Examiner—Marian C. Knode
Assistant Examiner—Thuan D. Dang
Attorney, Agent, or Firm—Frommer Lawrence & Haug

[57] ABSTRACT

This invention relates to a method for the selective preparation of a styrene of formula (1)

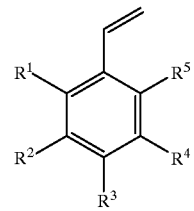

(1)

by reacting an acetophenone of formula (1)

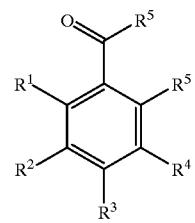

(2)

with hydrogen in the presence of a catalyst containing one of several oxides, in particular metal oxides, wherein the oxide contains an element form the groups Ia, IIa, IIIa, IVa, VIa, Ib, IIb, IVb, Vb, VIb, and/or VIII or an element from the lanthanide group. The catalyst contains preferably on or several oxides of the formula $ZnM^1{}_bM^2{}_cO_x$, where $M^1$ stands for at least one element from the Al, Zr, Ti and Si group, $M^2$ stands for at least one element from the Cd, Cu, Ag, Ni, Co, Fe, Mn, Cr, Mo, Ta, Sc, W, V, Nb, Hf, Yt, B, In, Zn, Pb, Bi Se, Ga, Ge, Sb, As, Te group, or an element from the lanthanides, b=0–20, c=0–3, x corresponds to the number of oxygen atoms required for stoechiometric compensation, which results in accordance with the oxidation states of Zn, $M^1$ and $M^2$ or oxides of formula $M^3{}_2M^4O_4$, wherein $M^3$ is an element with an oxidation state I, II or III and $M^4$ is an element with oxidation state II, III or VI.

11 Claims, No Drawings

METHOD FOR PREPARATION OF STYRENES

CROSS-REFERENCES TO RELATED APPLICATIONS

This application was filed pursuant to 35 USC § 371 and was filed on Jan. 17, 1998 as International Patent Application PCT/EP/98 00244, which in term claims priority under 35 USC § 119 to German application 19 703 11 1.0, filed Jan. 29, 1997.

STATEMENT REGARDING FEDERALLY SPONSORED RESEARCH OR DEVELOPMENT

Not Applicable. BACKGROUND OF THE INVENTION

1. Field of the Invention

The present invention relates to a technically simple process for preparing substituted styrenes in the presence of oxide catalysts, in particular metal oxide catalysts.

2. Description of the Related Art

Owing to the great importance of substituted styrenes in industrial and preparative chemistry, e.g. use as monomers and as copolymers in the preparation of polystyrene (e.g. the preparation of p-hydroxystyrene (ACS Symp. Ser. 412 (1989)), there are numerous methods for preparing them. However, the processes for the targetted preparation of pure, isomer-free, substituted styrenes are, if available, frequently not optimum.

Thus, for example, it is known that styrene can be prepared from methyl halides and substituted toluenes above 700° C. in the gas phase (U.S. Pat. No. 3,636,182). The high temperatures, up to 1200° C., necessary in the process described favor secondary reactions and also decomposition reactions. Furthermore, hydrochloric acid is formed during the reaction, so that the reactor has to be made of materials which are not attacked even under these extreme conditions. Particular disadvantages are the incomplete conversion and the low selectivity of the process disclosed here.

Furthermore, substituted styrenes can also be prepared from ethyl-benzenes by catalytic dehydrogenation (DE-A 2 317 525). Disadvantages of this process are the usually incomplete conversion of the starting material and the associated separation of the unreacted starting material from the product by distillation. Dehydrogenations of the type described here can only be carried out in special apparatuses and, in addition, ethyl-benzenes are not readily available in industrial amounts.

The preparation of p-substituted styrene derivatives by 1. reaction of para-substituted benzyl halides with triphenylphosphine in chloroform and 2. subsequent reaction with formaline solution and sodium hydroxide is described in Synth. Commun. 6(1976)53. Since the reaction is carried out in solution, this process too results in separation problems during the isolation of the final product after the reaction is complete.

The processes described in the prior art do not give satisfactory results in respect of the conversion of the starting materials or the selectivity of the reaction. Furthermore, the processes described are often associated with high temperatures and a relatively high cost for isolating the pure product.

It is therefore an object of the invention to find a simple and economical process for the selective preparation of styrenes which avoids the disadvantages known from the prior art.

BRIEF SUMMARY OF THE INVENTION

It has now been found that acetophenones can be converted into styrenes in one reaction step by means of hydrogen over an oxide catalyst.

The present invention accordingly provides a process for the selected preparation of a styrene of the formula (1)

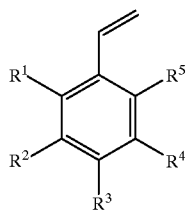

(1)

by reaction of an acetophenone of the formula (2)

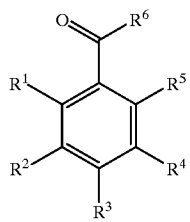

(2)

with hydrogen in the presence of a catalyst comprising one or more oxides, in particular metal oxides, where the oxide comprises an element of groups Ia, IIa, IIIa, IVa, Va, VIA, Ib, IIb, IIIb, IVb, Vb, VIb, VIIb and/or VIII or an element of the lanthanide series. The radicals $R^1$, $R^2$, $R^3$, $R^4$, $R^5$ and $R^6$ in the formulae (1) and (2) are identical or different and are each H, F, Cl, Br or I or a $C_1$–$C_{30}$-group which may contain heteroatoms, in particular a ($C_1$–$C_{20}$)-alkyl, ($C_6$–$C_{14}$)-aryl, ($C_1$–$C_{10}$)-alkoxy, ($C_2$–$C_{10}$)-alkenyl, ($C_7$–$C_{20}$)-arylalkyl, ($C_7$–$C_{20}$)-alkylaryl, ($C_6$–$C_{10}$)-aryloxy, ($C_1$–$C_{10}$)-fluoroalkyl, ($C_6$–$C_{10}$)-haloaryl or ($C_2$–$C_{10}$)-alkynyl group or an —$SiR^7_3$ radical, where $R^7$ is ($C_1$–$C_{10}$)-alkyl, or two or more of the radicals $R^1$ to $R^5$ together with the atoms connecting them form one or more substituted or unsubstituted rings or $R^4$ and $R^5$ together form an aromatic ring.

Examples of heteroaromatic radicals are thienyl, furyl and pyridyl.

The rings formed by adjacent radicals $R^1$ to $R^7$ may also be substituted by substituents defined as for $R^1$ to $R^6$, including the preferred ranges mentioned for these.

In the formula (1), it is preferred that $R^1$, $R^2$, $R^3$, $R^4$ and $R^5$ are identical or different and are hydrogen, ($C_6$–$C_{10}$)-aryl or ($C_1$–$C_{10}$)-alkyl or the radicals $R^1$ and $R^2$, $R^2$ and $R^3$, $R^3$ and $R^4$ or $R^4$ and $R^5$ together with the atoms connecting them form a substituted or unsubstituted, six-membered, saturated or unsaturated carbocycle. $R^3$ is preferably isopropyl and $R^6$ is preferably methyl.

The saturated or unsaturated, five- or six-membered ring (carbocycle) formed by adjacent substituents $R^1$–$R^4$ may additionally bear substituents, preferably ($C_1$–$C_{10}$)-alkyl.

Examples of styrenes of the formula (2) are styrene, 2-isobutylstyrene, 3-isobutylstyrene, 3-isobutyl-1-methylstyrene, 4-isobutylstyrene, 4-isobutylmethylstyrene, 4-isobutylphenylstyrene, 2-isopropylstyrene, 2-isopropyl-5-methylstyrene, 4-isopropylstyrene, 4-isobutylphenylstyrene, 4-isobutyl-3-methylstyrene, 5-isopropyl-3-methylstyrene, 5-isopropyl-2-methylstyrene, vinyinaphthalene and 4-methylvinyinaphthalene.

As catalyst, preference is given to ones which comprise one or more oxides of the formula (3),

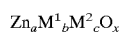

where $M^1$ is at least one element selected from the group consisting of Al, Zr, Ti and Si;

$M^2$ is at least one element selected from the group consisting of Cd, Cu, Ag, Ni, Co, Fe, Mn, Cr, Mo, Ta, Sc, W, V, Nb, Hf, Yt, B, In, Zn, Pb, Bi, Se, Ga, Ge, Sb, As, Te and the lanthanide elements. The indices a, b, c and x are gram atom ratios and are preferably in the following ranges:

a=1, b=0–20, in particular 0.01–15, c=0–3, in particular from 0.01 to 2.5, and x is the number of oxygen atoms necessary to balance the charge, which is determined by the oxidation states of Zn, $M^1$ and $M^2$.

In a further preferred embodiment of the present invention, the oxides of the formula (3) in the catalyst can be replaced by oxides of the formula (4), $$M^3{}_2M^4O_4$$

which are double oxides from the class of spinels (Chemie der Elemente, N. N. Greenwood, A. Earnshaw, VCH-Verlagsgesellschaft mbH, Weinheim, 1990; Lehrbuch der Anorganischen Chemie, A. F. Holleman, N. Wiberg, de Gruyter, Berlin, 1985). In formula (4), $M^3$ and $M^4$ may be any elements of the Periodic Table of the Elements, where $M^3$ is an element in the oxidation state I, II or III and $M^4$ is an element in the oxidation state II, III or VI. Preference is given to the following situation: when $M^3$ is an element in the oxidation state I, $M^4$ is in the oxidation state VI; when $M^3$ is an element in the oxidation state II, $M^4$ is in the oxidation state IV and when $M^3$ is an element in the oxidation state II, $M^4$ is in the oxidation state II. It is likewise possible for $M^3$ and $M^4$ to be the same element as long as it can be present in the appropriate, different oxidation states.

In particular, the catalyst comprises the following oxides of the formula (4):

$$Al_2ZnO_4, Al_2CoO_4, Al_2MnO_4, Al_2FeO_4, \text{ and } Cr_2FeO_4.$$

The catalysts used according to the present invention have been described in the German Application P 196 088 14.3 (HOE 96/F 054), which has earlier priority but is not a prior publication, for the preparation of indenes from indanone.

The catalyst used according to the invention may comprise an inorganic or organic support material. As support materials, preference is given to using the following materials: aluminium oxides, silicon dioxide, aluminosilicates, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, silicon nitride or silicon carbide or polypyridines or polyacrylates.

The catalyst can be prepared by impregnation of a support or shaped body or by coprecipitation followed by drying and calcination. A further possibility is the direct calcination of suitable metal compounds, e.g. of nitrates, acetates, carbonates or other salts and complexes of the elements $M^1$ to $M^4$.

For the impregnation of supports, a solution of compounds of the elements $M^1$ to $M^4$ can be applied to a support which is preferably inorganic and may, for example, consist of $SiO_2$, SiC, $Al_2O_3$, $Al(OH)_3$, $ZrO_2$, aluminosilicates, SiN or $TiO_2$. Compounds of the elements $M^1$ to $M^4$ which are suitable for impregnation are, for example, their halides, nitrates, sulfates, oxalates, carboxylates and alkoxides. The impregnated supports are subsequently dried at from 100° C. to 170° C., preferably from 120° C. to 150° C., and calcined at 400–1000° C., preferably from 500 to 800° C. The catalysts which have been prepared in this way can be further processed by customary methods before or after calcination to produce pellets, tablets or extrudates.

For coprecipitation, suitable compounds of the elements $M^1$ to $M^4$ can be precipitated at appropriate pH values. After the precipitation, the hydroxides formed are filtered off and washed with a suitable solvent.

Drying is carried out at from 100 to 170° C., preferably from 120° C. to 150° C., at atmospheric pressure or under reduced pressure; calcination is carried out at from 400 to 1000° C., preferably from 500 to 900° C. The catalyst which has been prepared in this way is in the form of granules and, after comminution to the desired particle size, can be used directly in the reaction.

Prior to use in the process of the invention, the catalyst can be preactivated at temperatures of from 100 to 800° C. using a suitable reducing agent.

The process of the invention can be carried out continuously or batchwise in a suitable reactor. In the process of the invention, preference is given to reacting compounds of the formula (2) at a temperature in the range from 200 to 600° C., in particular from 250 to 400° C., and a pressure in the range from 0.1 to 10 bar, in particular at atmospheric pressure, in the presence of a catalyst comprising compounds of the formula (3) or compounds of the formula (4) to give compounds of the formula (1). The reaction times are usually in the range from 0.5 to 10 hours, in particular in the range from 1 to 6 hours.

The present process can be carried out using molecular hydrogen which may also be prepared in situ. It is also possible to dilute the hydrogen with an inert gas such as nitrogen or argon. The acetophenone used according to the invention can be used as a solid, as a melt, as a liquid or as a solution in a suitable solvent such as benzene, xylene, toluene or cyclohexane. Preferably, isopropylacetophenone is fed to a vaporizer and is subsequently brought into contact in the gas phase with the catalyst used according to the invention. The molar ratio of the acetophenone to hydrogen is preferably from 1:1 to 1:500, particularly preferably from 1:2 to 1:50. The feed rate for the acetophenones is preferably from 0.01 to 20 g/ml of catalyst (LHSV: liquid hourly space velocity), particularly preferably from 0.2 to 10 g/ml of catalyst. The feed rate of the hydrogen is preferably from 50 to 50,000 h$^{-1}$ (GHSV: gas hourly space velocity), particularly preferably from 100 to 10,000 h$^{-1}$.

The styrenes prepared using the process described can be freed of by-products by distillation, column chromatography or crystallization.

Unlike the known processes for preparing styrene, the process of the invention makes it possible to obtain pure, isomer-free styrene in one step from readily available starting materials. Since the process is carried out under relatively mild reaction conditions, the formation of undesired by-products or decomposition products is minimized. The styrenes obtained according to the invention can be separated from the reaction mixture and subsequently purified without great expense.

The process described makes it possible to prepare styrenes of the formula (1) with a selectivity in the range from 80 to 100%, in particular from 85 to 99%. The conversions of acetophenone are here usually in the range from 80 to 100%, in particular in the range from 85 to 97%.

The invention is illustrated by the following examples. However, the scope of the examples described has no limiting character:

EXAMPLES

Example 1

139.0 g of $Al(NO_3)_3 \times 9$ $H_2O$ and 55.0 g of $Zn(NO_3)_2 \times 6$ $H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 2

69.5 g of $Al(NO_3)_3 \times 9\ H_2O$ and 110.0 g of $Zn(NO_3)_2 \times 6\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 3

139.0 g of $Al(NO_3)_3 \times 9\ H_2O$ and 110.0 g of $Zn(NO_3)_2 \times 6\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 4

139.0 g of $Al(NO_3)_3 \times 9\ H_2O$ and 54.9 g of $Zn(NO_3)_2 \times 6\ H_2O$ and 2.2 g of $Co(NO_3)_3$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 5

139.0 g of $Al(NO_3)_3 \times 9\ H_2O$ and 54.9 g of $Zn(NO_3)_2 \times 6\ H_2O$ and 1.35 g of $Cu(NO_3)_2 \times 3\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 6

139.0 g of $Al(NO_3)_3 \times 9\ H_2O$ and 54.9 g of $Zn(NO_3)_2 \times 6\ H_2O$ and 2.23 g of $Cr(NO_3)_3 \times 9\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 7

139.0 g of $Al(NO_3)_3 \times 9\ H_2O$ and 54.9 g of $Zn(NO_3)_2 \times 6\ H_2O$ and 1.62 g of $Ni(NO_3)_2 \times 6\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 8

139.0 g of $Al(NO_3)_3 \times 9\ H_2O$ and 54.9 g of $Zn(NO_3)_2 \times 6\ H_2O$ and 1.40 g of $Mn(NO_3)_3 \times 4\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 9

139.0 g of $Al(NO_3)_3 \times 9\ H_2O$ and 54.9 g of $Zn(NO_3)_2 \times 6\ H_2O$ and 2.03 g of $Y(NO_3)_3 \times 6\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 10

139.0 g of $Al(NO_3)_3 \times 9\ H_2O$ and 54.9 g of $Zn(NO_3)_2 \times 6\ H_2O$ and 2.25 g of $Fe(NO_3)_3 \times 9\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 11

139.0 g of $Al(NO_3)_3 \times 9\ H_2O$ and 54.9 g of $Zn(NO_3)_2 \times 6\ H_2O$ and 2.42 g of $Ce(NO_3)_3 \times 6\ H_2O$ are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Example 12

139.0 g of $Al(NO_3)_3 \times 9\ H_2O$ and 54.9 g of $Zn(NO_3)_2 \times 6\ H_2O$ and 1.16 g of tetraethoxysilane are dissolved in 3.8 l of water and cooled to 5° C. The pH is adjusted to 9 using 25% strength ammonia solution. The precipitate is filtered off and washed with water. Drying is carried out at 130° C. and calcination at 600° C. After comminution to particle sizes of from 10 to 20 mesh, the catalyst is preactivated at 450° C. in a stream of hydrogen.

Examples 13–18

In a tube reactor, 4-isopropylacetophenone was reacted with hydrogen in the presence of the catalyst from Examples 1–4 to form 2-isopropylstyrene. The bed volume of the catalyst used was 20 ml. The vaporization of the 4-isopropylacetophenone used was carried out in an upstream vaporizer. The GHSV (gas hourly space velocity), LHSV (liquid hourly space velocity) and reaction temperature are shown in Table 1. The reaction product was condensed by means of a condenser and analyzed by gas chromatography.

TABLE 1

| Ex. | Catalyst from Ex. | GHSV | LHSV | Temperature | Conversion | Selectivity |
|---|---|---|---|---|---|---|
| 13 | 1 | 25 | 5 | 300 | 100 | 88 |
| 14 | 2 | 25 | 4.5 | 330 | 100 | 86 |
| 15 | 3 | 25 | 5.5 | 330 | 100 | 87 |
| 16 | 4 | 25 | 9.5 | 330 | 100 | 85 |
| 17 | 1 | 25 | 10 | 350 | 100 | 87 |
| 18 | 2 | 25 | 7.5 | 300 | 100 | 78 |
| 19 | 3 | 25 | 2.6 | 350 | 100 | 91 |
| 20 | 4 | 25 | 2.5 | 300 | 100 | 74 |

Examples 19–20

In a tube reactor, 4-isobutylacetophenone was reacted with hydrogen in the presence of the catalysts from Examples 3 and 4 to form 2-isobutylstyrene. The bed volume of the catalyst used was 20 ml. The vaporization of the 4-isobutylacetophenone used was carried out in an upstream vaporizer. The GHSV, LHSV and reaction temperature are shown in Table 1. The reaction product was condensed by means of a condenser and analyzed by gas chromatography.

Examples 21–22

In a tube reactor, 4-isobutylacetophenone was reacted with hydrogen in the presence of ZnO to form 2-isobutylstyrene. The bed volume of the catalyst used was 20 ml. The vaporization of the 4-isobutylacetophenone used was carried out in an upstream vaporizer. The GHSV, LHSV and reaction temperature are shown in Table 2. The reaction product was condensed by means of a condenser and analyzed by gas chromatography.

TABLE 2

| Ex. | Catalyst | GHSV | LHSV | Temperature | Conversion | Selectivity |
|---|---|---|---|---|---|---|
| 21 | ZnO | 25 | 2.7 | 350 | 100 | 95 |
| 22 | ZnO | 25 | 2.3 | 300 | 100 | 99 |

What is claimed is:

1. A process for the selected preparation of a styrene of the formula (1)

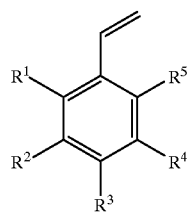

(1)

by reacting an acetophenone of the formula (2)

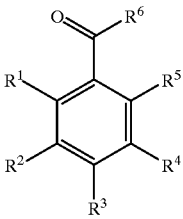

(2)

where $R^1$, $R^2$, $R^3$, $R^4$, $R^5$ and $R^6$ are identical or different and are each H, F, Cl, Br or I or a $C_1$–$C_{30}$-group, which optionally contains heteroatoms, or two or more of the radicals $R^1$ to $R^5$ together with the atoms connecting them optionally forms one or more substituted or unsubstituted rings, with hydrogen in the presence of a catalyst comprising one or more oxides has the formula (3)

$$Zn_a M^1{}_b M^2{}_c O_x$$

where
  $M^1$ is at least one element selected from the group consisting of Al, Zr, Ti and Si;
  $M^2$ is at least one element selected from the group consisting of Cd, Cu, Ag, Ni, Co, Fe, Mn, Cr, Mo, Ta, Sc, W, V, Nb, Hf, Yt, B, In, Pd, Bi, Se, Ga, Ge, Sb, As, Te, and the lanthanide elements,
  B is 0–2,
  C is 0–3, and
  X is the number of oxygen atoms necessary to balance the charge which is determined by the oxidation states of Zn, $M^1$ and $M^2$ or a catalyst has the formula (4)

$$M^3{}_2 M^4 O_4 \qquad (4)$$

where
  $M^3$ is an element in the oxidation state I and
  $M^4$ is an element in the oxidation state VI.

2. The process as claimed in claim 1, wherein the catalyst comprises compounds of the formulae $Al_2ZnO_4$, $Al_2CoO_4$, $Al_2MnO_4$, $Al_2FeO_4$, $Al_2NiO_4$, and/or $Cr_2FeO_4$.

3. The process as claimed in claim 1, wherein the catalyst comprises an inorganic or organic support material.

4. The process as claimed in claim 3, wherein the inorganic or organic support material is selected from the group consisting of aluminium oxides, silicon dioxide, aluminosilicates, titanium dioxide, zirconium dioxide, thorium dioxide, lanthanum oxide, magnesium oxide, calcium oxide, barium oxide, tin oxide, cerium dioxide, boron oxide, boron nitride, boron carbide, boron phosphate, zirconium phosphate, silicon nitride, silicon carbide, polypyridines, and polyacrylates.

5. The process as claimed in claim 1, wherein the selectivity in the preparation of compounds of the formula (1) is in the range from 80 to 100%.

6. The process as claimed in claim 1, wherein compounds of the formula (2) are reacted with hydrogen at a temperature in the range from 200 to 600° C. and a pressure in the range from 0.1 to 10 bar in the presence of a catalyst comprising compounds of the formula (3) or compounds of the formula (4).

7. The process as claimed in claim 1, wherein the molar ratio of compounds of the formula (2) to hydrogen is in the range from 1:1 to 1:500.

8. The process as claimed in claim 1, wherein the feed rate of the hydrogen is in the range from 50 to 50,000 h$^{-1}$ (GHSV: gas hourly space velocity).

9. The process as claimed in claim 1, wherein the compound of the formula (1) is styrene, 2-isobutylstyrene, 3-isobutylstyrene, 3-isobutyl-1-methylstyrene, 4-isobutylstyrene, 4-isobutylmethylstyrene, 4-isobutylphenylstyrene, 2-isopropylstyrene, 2-isopropyl-5-methylstyrene, 4-isopropylstyrene, 4-isobutylphenylstyrene, 4-isobutyl-3-methylstyrene, 5-isopropyl-3-methylstyrene, 5-isopropyl-2-methylstyrene, vinylnaphthalene or 4-methylvinylnaphthalene.

10. The process as claimed in claim 1, wherein the conversion of compounds of the formula (2) is in the range from 80 to 100%.

11. The process according to claim 1 herein $R^1$, $R^2$, $R^3$, $R^4$, $R^5$ and $R^6$ are identical or different and are each H, F, Cl, Br, I, $(C_1-C_{20})$-alkyl, $(C_6-C_{14})$-aryl, $(C_1-C_{10})$-alkoxy, $(C_2-C_{10})$-alkenyl, $(C_7-C_{20})$-arylalkyl, $(C_7-C_{20})$-alkylaryl, $(C_6-C_{10})$-aryloxy, $(C_1-C_{10})$-fluoroalkyl, $(C_6-C_{10})$-haloaryl or $(C_2-C_{10})$-alkynyl group or an —$SiR^7{}_3$ radical, where $R^7$ is $(C_1-C_{10})$-alkyl.

* * * * *